United States Patent
Shi et al.

(10) Patent No.: US 12,064,608 B2
(45) Date of Patent: Aug. 20, 2024

(54) ROTATIONAL LOCKING TYPE SAFETY INSULIN PEN NEEDLE

(71) Applicant: SANDSTONE MEDICAL (SUZHOU) INC., Jiangsu (CN)

(72) Inventors: Guoping Shi, Suzhou (CN); Anthony Scott Horstman, Suzhou (CN)

(73) Assignee: SANDSTONE MEDICAL (SUZHOU) INC., Suzhou (CN)

( * ) Notice: Subject to any disclaimer, the term of this patent is extended or adjusted under 35 U.S.C. 154(b) by 905 days.

(21) Appl. No.: 17/256,887

(22) PCT Filed: Jun. 29, 2019

(86) PCT No.: PCT/CN2019/094030
§ 371 (c)(1),
(2) Date: Dec. 29, 2020

(87) PCT Pub. No.: WO2020/001656
PCT Pub. Date: Jan. 2, 2020

(65) Prior Publication Data
US 2021/0138159 A1 May 13, 2021

(30) Foreign Application Priority Data
Jun. 29, 2018 (CN) .......................... 201810694474.9

(51) Int. Cl.
*A61M 5/32* (2006.01)
*A61M 5/31* (2006.01)

(52) U.S. Cl.
CPC ........ *A61M 5/3202* (2013.01); *A61M 5/3134* (2013.01)

(58) Field of Classification Search
CPC ........ A61M 5/3257; A61M 2005/3254; A61M 5/326; A61M 5/3245; A61M 2005/3247; A61M 2005/3267; A61M 5/3271
See application file for complete search history.

(56) References Cited

U.S. PATENT DOCUMENTS

2009/0259196 A1* 10/2009 Gratwohl .............. A61M 5/326
604/198
2013/0245562 A1 9/2013 Kouyoumjian et al.

FOREIGN PATENT DOCUMENTS

| CN | 104307072 A | 1/2015 |
| CN | 204395141 U | 6/2015 |
| CN | 104771813 A | 7/2015 |
| CN | 108186029 A | 6/2018 |
| CN | 108992744 A | 12/2018 |

OTHER PUBLICATIONS

Oct. 22, 2019 Search Report issued in International Patent Application No. PCT/CN2019/094030.

* cited by examiner

*Primary Examiner* — Courtney B Fredrickson
(74) *Attorney, Agent, or Firm* — Oliff PLC

(57) ABSTRACT

A safety insulin pen needle includes a needle body, intermediate shield, front shield, tail cover, rear spring, and rotating tube. The rotating tube includes a beveled rail, and the front shield includes a bevel acting part that interacts with the beveled rail. The tail cover includes an elastic leg, which includes a rear protection stopper. The rotating tube includes a first and second rail slot spaced apart along a circumferential direction, which interact with the rear protection stopper. Backward movement of the front shield when the needle is pushed rotates the rotating tube and uses the interaction of the first and second rail slot on the rotating tube and the rear protection stopper on the tail cover to change the relationship between the tail cover and the rotating tube, which provides reliable locking protection of the tail cover after use.

8 Claims, 11 Drawing Sheets

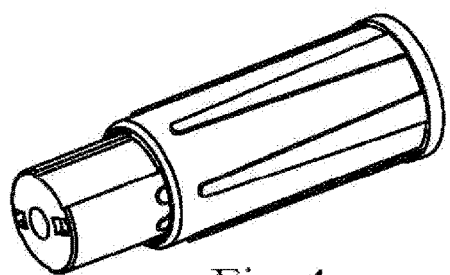
Fig. 1
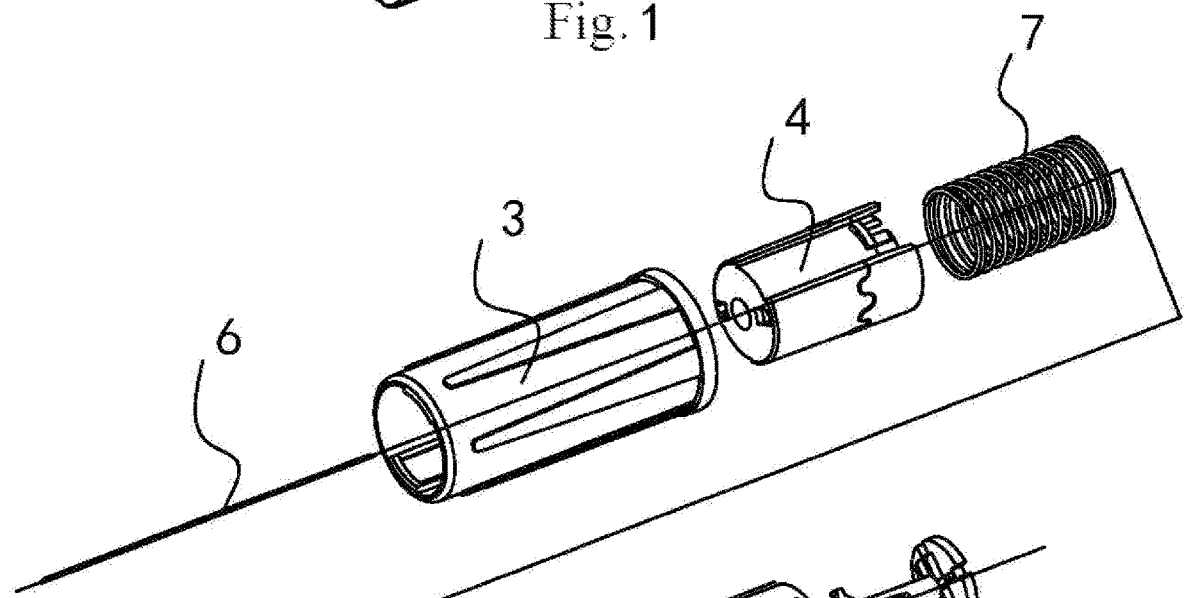
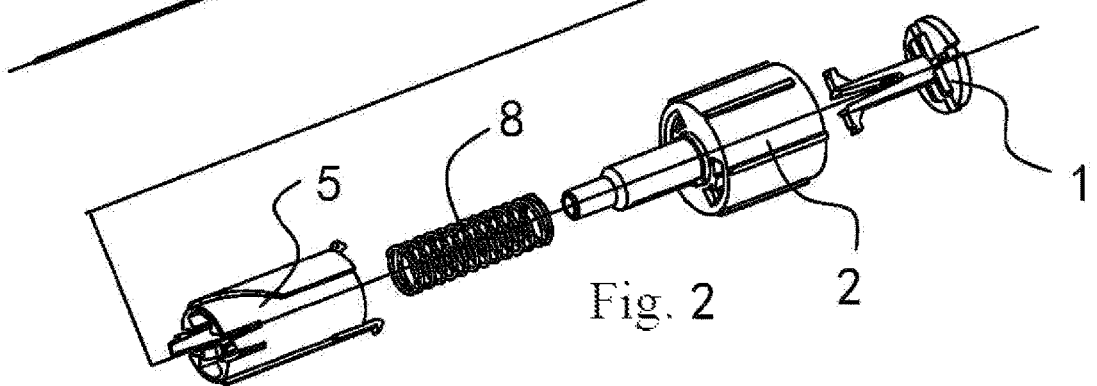
Fig. 2

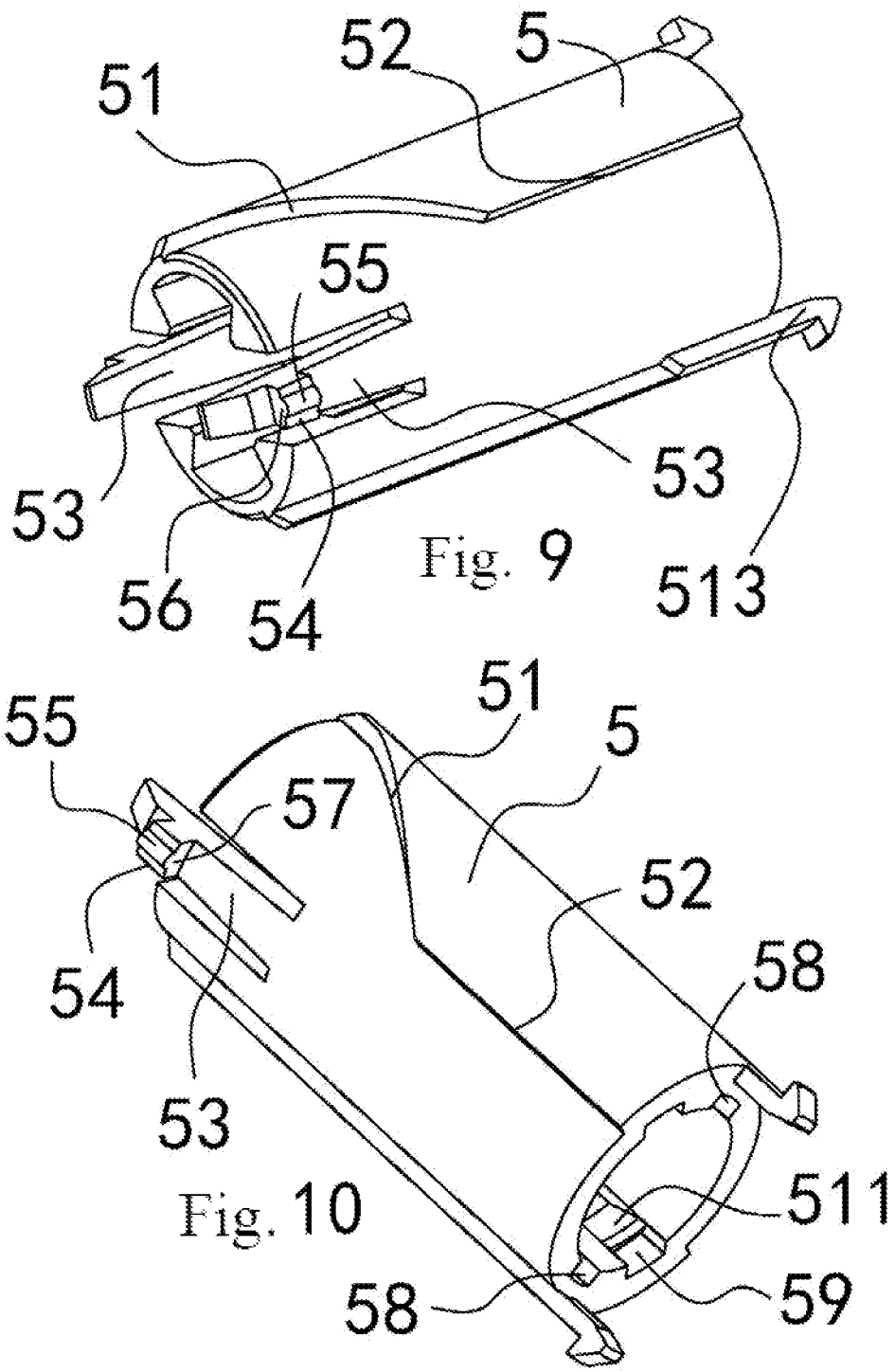

C-C

D-D

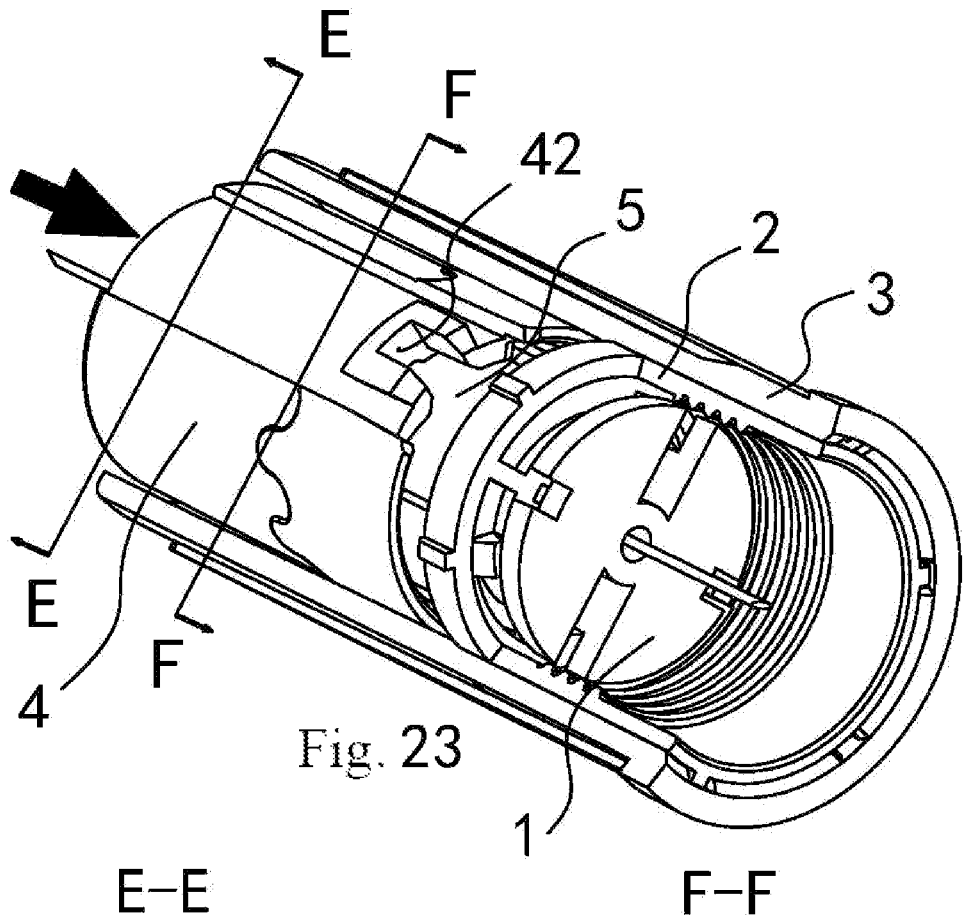
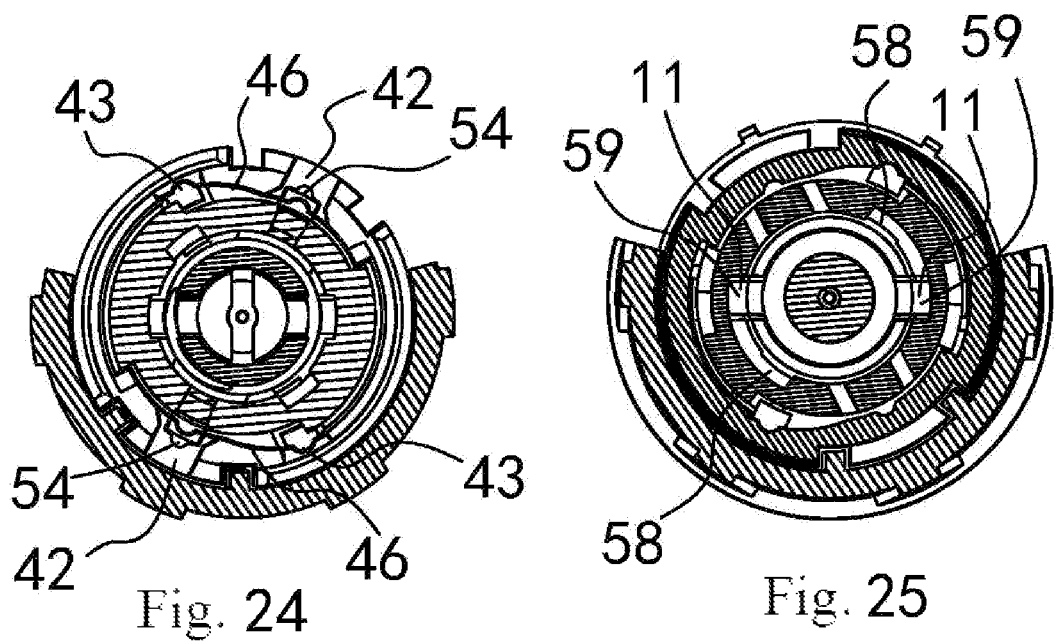
Fig. 23
Fig. 24
Fig. 25

ROTATIONAL LOCKING TYPE SAFETY INSULIN PEN NEEDLE

TECHNICAL FIELD

The present invention relates to a medical insulin injection tool, especially a rotational locking type safety insulin pen needle. This injection needle could be used with the insulin pen to inject by oneself or by others, while the insulin pen could be reused and the injection needle is disposable. The injection needle of the present invention is characterized in that it makes use of the puncturing action to rotationally lock the rotating part to provide the safety protection for the needle tip after the use.

BACKGROUND OF INVENTION

Diabetes is a metabolic disease characterized by high blood sugar, and there is no radical cure to it, but the injection of insulin to the patients could effectively control the disease.

The insulin injection tools are diversified and the insulin injection needle mentioned in the present invention is an injection tool used with the insulin pen, which could carry a prescribed amount of insulin liquid medicine and could be reused, while the injection needle is a disposable needle with safety protection device.

The Chinese patent CN204395141U announced and authorized a utility model patent titled with "A safety insulin pen needle". The patent relates to insulin injection needle, which has the following disadvantages although its structure is simple: 1. Because the structure is too simple, it can not guarantee its stability and reliability; 2. After the product is used, only the front end protection is available and the rear end protection is not available, and even if the rear end protection is set, the linkage with the front end protection is not available; 3. The locking of the front end protection structure is directional, so its locking stability and reliability are not high.

Therefore, the present invention is aimed to design an insulin pen needle with simple structure, stable operation and reliable locking protection from the perspective of safety and reliability of its use.

DISCLOSURE OF THE INVENTION

In view of the disadvantages of the prior art, the present invention provides a rotational locking type safety insulin pen needle, which aims to provide the reliable locking protection on the basis of simple structure and stable work.

In order to achieve the above object, the present invention applies the following technical solution: a rotational locking type safety insulin pen needle comprising:

A needle body with an injection section at the frond end and a connecting section at the rear end.

An intermediate shield of tube structure, provided with a through hole at its front end and connected or provided with a structure to connect the insulin pen at the rear end.

A front shield, used to protect the injection section of the needle body, and the main structure of the front shield is a tubular body.

A tail cover, a component to protect the connecting section of the needle body.

A rear spring, used to push the tail cover to the protection position of the connecting section of the needle body.

Wherein: it comprises a rotating tube, and the main structure of the rotating tube is a tubular body, and the tubular body of the rotating tube is provided with a beveled rail on the outer edge, and the beveled rail is composed of a section of bevel or spiral surface as the guiding surface relative to the axis of the tubular body.

The front shield is provided with a bevel acting part on its inner edge relative to the beveled rail on the rotating tube.

The tail cover is composed of a cap and an elastic leg, and the cap is an end cap or a ring body, and the cap is provided with a cannula passing hole only for insertion of the connecting section of the needle body at the center, and the rear part of the elastic leg is fixedly connected with the cap, and the elastic leg is provided with a rear protection stopper in the front and the front end face of the rear protection stopper is the front stopping face of rear stopper.

Relative to the rear protection stopper on the tail cover, the tubular body of the rotating tube is provided with a first rail slot and a second rail slot on the inner edge, and the first rail slot and the second rail slot are arranged in parallel along the axial direction of the tubular body of the rotating tube and are arranged at intervals along the circumferential direction of the tubular body of the rotating tube; and a transverse channel is arranged circumferentially on the inner edge of the tubular body in the front of the first rail slot and the second rail slot.

In the assembly state before use, the needle body is located in the intermediate shield, and is positioned and fixed relative to the intermediate shield; the rotating tube is located in the intermediate shield, and is axially positioned and connected relative to the intermediate shield, and is rotationally connected circumferentially; the rear part of the front shield extends into the intermediate shield and is sleeved outside the rotating tube, and the front part of the front shield extends out of the through hole at the front end of the intermediate shield, and the front shield and the intermediate shield are slidably connected in the axial direction, and the front shield is provided with a front end limit moving forward relative to the intermediate shield; the bevel acting part on the inner edge of the front shield is located on the beveled rail; the tail cover is located in the intermediate shield and the connecting section of the needle body is inserted in the cannula passing hole of the tail cover; the rear protection stopper on the tail cover is located in the first rail slot of the rotating tube; the rear spring is located in the intermediate shield, the front end of the rear spring is positioned relative to the intermediate shield and the rear end of the rear spring is against the tail cover.

In the use state, when the insulin pen needle is pushed, the front shield moves backward axially relative to the intermediate shield, and the bevel acting part on the inner edge of the front shield and the beveled rail on the outer edge of the rotating tube coordinate with each other to force the rotating tube to rotate in the circumferential direction relative to the front shield, and the rear protection stopper on the elastic leg of the tail cover slides laterally to the second rail slot along the transverse channel; when the insulin pen exits the intermediate shield, the rear spring pushes the tail cover to move backward, and at the same time, the rear protection stopper on the elastic leg of the tail cover moves backward along the second rail slot. When the rear protection stopper moves backward along the second rail slot to the rear end limit position, the rear protection stopper upsprings, and at this time, the front stopping face of rear stopper on the rear protection stopper is against the rear end face of the second rail slot, so that the tail cover is axially positioned relative to the intermediate shield and enters the rear-end protection state.

The above described technical solution is explained as follows:

1. In above described technical solution, the "front" in the "front end", "front part", "front end face", "forward" and "front" refers to the direction of the needle tip of the injection section of insulin pen needle pointing to. The "rear" in said "rear end", "rear part" and "backward" means the direction opposite to the "front".

2. In above described technical solution, an external shield is provided on the outside of the intermediate shield, and the external shield is of the sleeve structure and is used to protect the integrity of insulin pen needle. As the external shield is irrelevant to the innovation point in the present invention, it is omitted in the text description and the drawings.

The design principle and effect of the invention are: the invention relates to a safety insulin pen needle which needs to be used with an insulin pen. In order to maintain the characteristics of simple structure and stable operation, while providing the reliable locking protection, the technical idea of the invention is as follows:

Firstly, a rotating tube is provided in the intermediate shield and a beveled rail is provided on the outer edge of the rotating tube; the front shield is provided with a bevel acting part on its inner edge relative to the beveled rail. When the insulin pen needle is pushed forward, the front shield moves backward and drives the rotation of the rotating tube.

Secondly, the tail cover is provided with an elastic leg and the elastic leg is provided with a rear protection stopper; relative to the rear protection stopper, the tubular body of the rotating tube is provided with a first rail slot and a second rail slot on the inner edge, and the first rail slot and the second rail slot are arranged in parallel along the axial direction of the tubular body of the rotating tube and are arranged at intervals along the circumferential direction of the tubular body of the rotating tube. In the assembly state before use, the rear protection stopper on the tail cover is located in the first rail slot of the rotating tube. In the use state, when the insulin pen needle is pushed, the front shield moves backward to drive the rotating tube to rotate, and the rear protection stopper on the tail cover slides laterally to the second rail slot along the transverse channel. When the insulin pen exits the intermediate shield, the rear spring pushes the tail cover to move backward, and when the rear protection stopper moves backward to the rear end position along the second rail slot, the rear protection stopper upsprings, and at this time, the front stopping face of rear stopper on the rear stopper is against the rear end face of the second rail slot, so that the tail cover is axially positioned and enters the rear-end protection state.

In short, the present invention uses the backward movement of the front shield when the insulin pen needle is pushed to drive the rotation of the rotating tube and uses the coordination of the first rail slot and the second rail slot on the rotating tube and the rear protection stopper on the tail cover to change the coordination relationship between the tail cover and the rotating tube, which effectively provides the reliable locking protection of the tail cover after use. The technical solution is ingenious and the design is reasonable with prominent substantive features and significant technological progress, which fully embodies the simplicity, stability and reliability of the safety protection structure design of insulin pen needle.

BRIEF DESCRIPTION OF THE DRAWINGS

FIG. 1 is the perspective view of the safety insulin pen needle in the embodiment of present invention;

FIG. 2 is the exploded view of the insulin pen needle in the embodiment of present invention;

FIG. 9 is the first perspective view of the rotating tube of an embodiment of present invention;

FIG. 10 is the second perspective view of the rotating tube of an embodiment of present invention;

FIG. 23 is the stereoscopic view of an embodiment of the present invention when the front shield is continuously pressed until the needle tip penetrates into the skin;

FIG. 24 is the E-E cross sectional view of FIG. 23;

FIG. 25 is the F-F cross sectional view of FIG. 23;

FIG. 29 is the section view of an embodiment of the present invention after it's pulled out of skin.

In the above described drawings:

Figure 3:
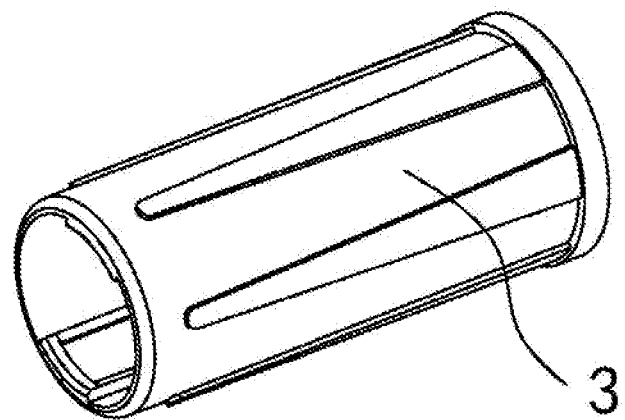
FIG. 3 is the first perspective view of the intermediate shield of an embodiment of present invention.
Figure 4:
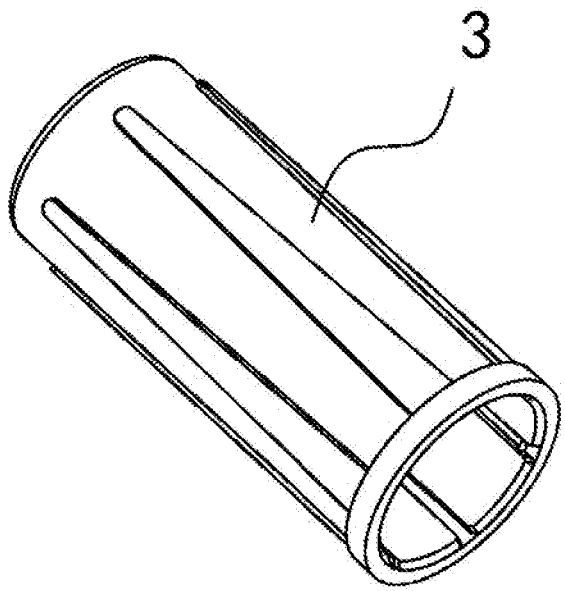
FIG. 4 is the second perspective view of the intermediate shield of an embodiment of present invention.
Figure 5:
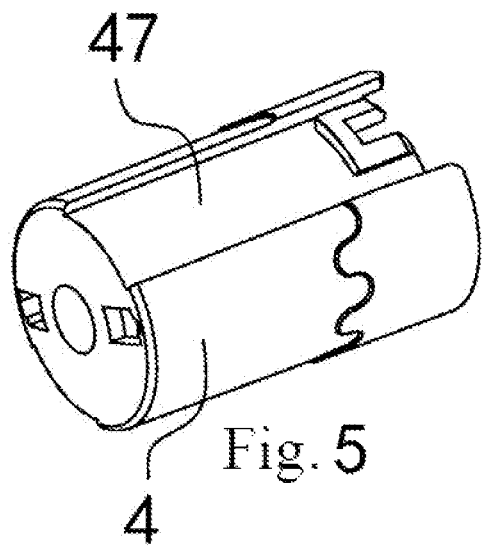
FIG. 5 is the first perspective view of the front shield of an embodiment of present invention.
Figure 6:
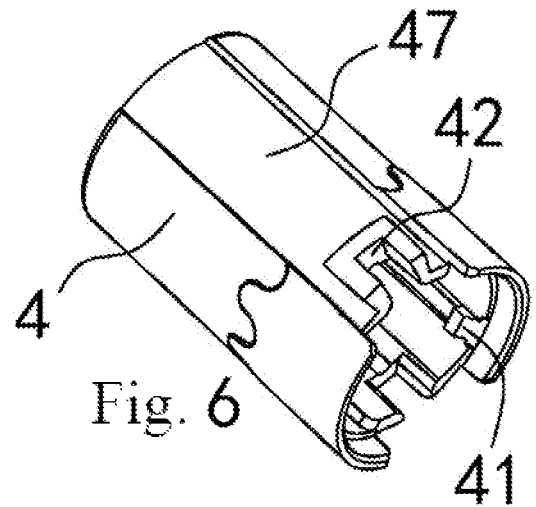
FIG. 6 is the second perspective view of the front shield of an embodiment of present invention.
Figure 7:
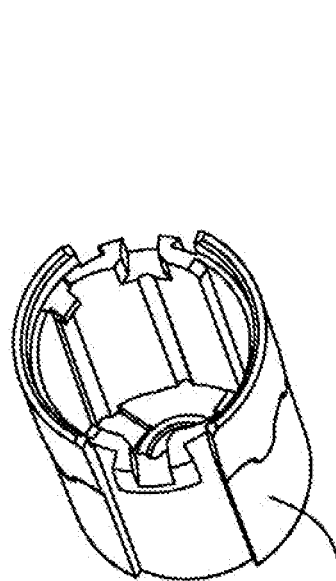
FIG. 7 is the third perspective view of the front shield of an embodiment of present invention.

1. Tail cover; 11. Rear protection stopper; 12. Front stopping face of rear stopper; 13. Rear stopping face of rear stopper; 14. Cap; 15. Elastic leg; 16. Cannula passing hole;
2. Threaded shield; 21. Needle base; 22. Shield; 23. Arc hole; 24. Slotted hole;
3. Intermediate shield;
4. Front shield; 41. Barb; 42. Stopping face; 43. Guiding slot; 44. Limit slot; 45. Bevel acting part; 46. Transition face; 47. Sliding channel;
5. Rotating tube; 51. Beveled rail; 52. Straight rail; 53. Elastic arm; 54. Front protection stopper; 55. Flange; 56. Front stopping face; 57. Rear stopping face; 58. First rail slot; 59. Second rail slot; 510. Front step; 511. Rear step; 512. Transverse channel; 513. Hook;
6. Needle body;
7. Front spring;
8. Rear spring.

SPECIFIC EMBODIMENT

With reference to the accompanying drawings and embodiment, the present invention will be described in detail.

Embodiment: A rotational locking type safety insulin pen needle (with front end and rear end needle tip protection)

As shown in FIG. 1-14, the insulin pen needle includes a needle body 6, an intermediate shield 3, a front shield 4, a front spring 7, a rotating tube 5, a rear spring 8, a threaded shield 2 and a tail cover 1 (see FIG. 2). The complete insulin pen needle is usually provided with an external shield (also known as a "big sheath"), and the external shield is of the sleeve structure, which is usually on the outside of the intermediate shield and is used to protect the integrity of insulin pen needle. As the external shield in the embodiment is irrelevant to the innovation point of the present invention, it is omitted in the following text description and the drawings.

The following is the description of the components of insulin pen needle in this embodiment:

1. Needle Body 6

The needle body 6 is the needle to inject the insulin and the needle body 6 has an injection section extending in a forward direction, a connecting section extending in a rearward direction and a fixing section between the injection section and the connecting section;

2. Intermediate Shield 3 and Threaded Shield 2

Figure 15:
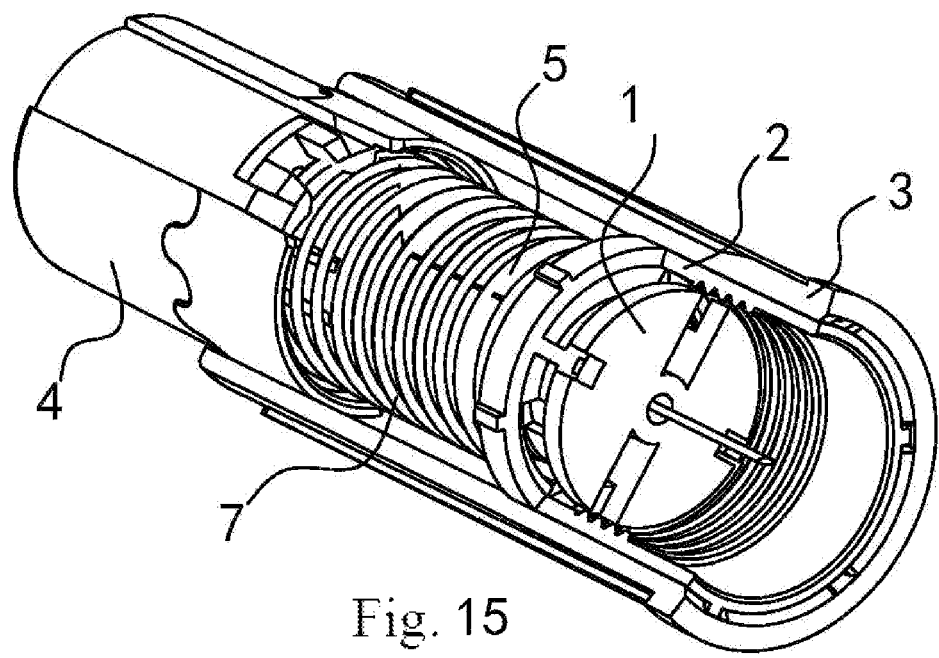
FIG. 15 is the stereoscopic view of an embodiment in initial state of the present invention.
Figure 16:
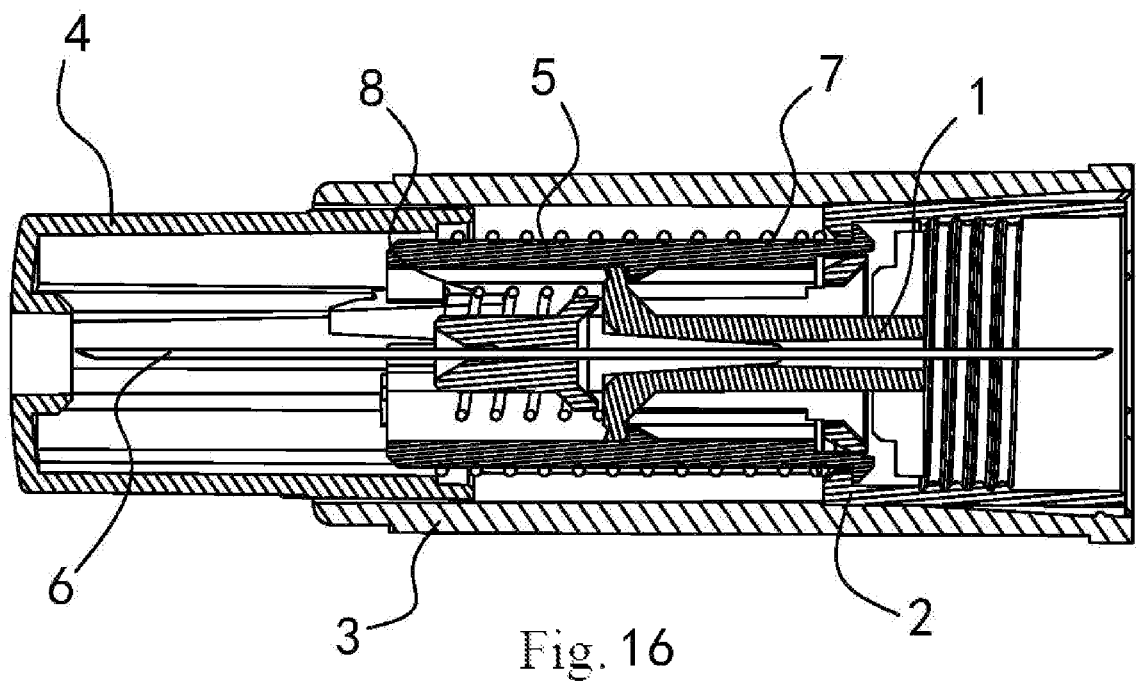
FIG. 16 is the section view of an embodiment in initial state of the present invention.

The intermediate shield 3 and the threaded shield 2 are fixed and assembled into a whole (see FIG. 15 and FIG. 16). The whole body is equivalent to the main cover in the insulin pend needle and is used to contain other parts (see FIG. 16). The intermediate shield 3 is of tube structure (see FIGS. 3 and 4), and the intermediate shield 3 is provided with a through hole at its front end and the intermediate shield 3 is fixedly sleeved outside the threaded shield 2 at its rear end. That is, the intermediate shield 3 is fixedly provided with a threaded shield 2, and the threaded shield 2 is composed of a needle base 21 and a shield 22 (see FIG. 12). The needle base 21 is fixedly connected at the front end of the shield 22, and the needle base 21 is used to fix the needle body 6, that is, the fixing section of the needle body 6 is fixed on the needle base 21 and the injection section of the needle body 6 extends from the front end of the needle base 21, and the connecting section of the needle body 6 extends from the rear end of the needle base 21. The shield 22 is provided with internal thread to connect an insulin pen on the inner edge. Actually, the rear end of the threaded shield 2 is used to connect the insulin pen and the connection structure may be the threaded connection, plug-in connection and plug-in turn buckle connection, etc. In this embodiment, the threaded shield 2 is the threaded connection.

3. Rotating Tube 5

Figure 11:
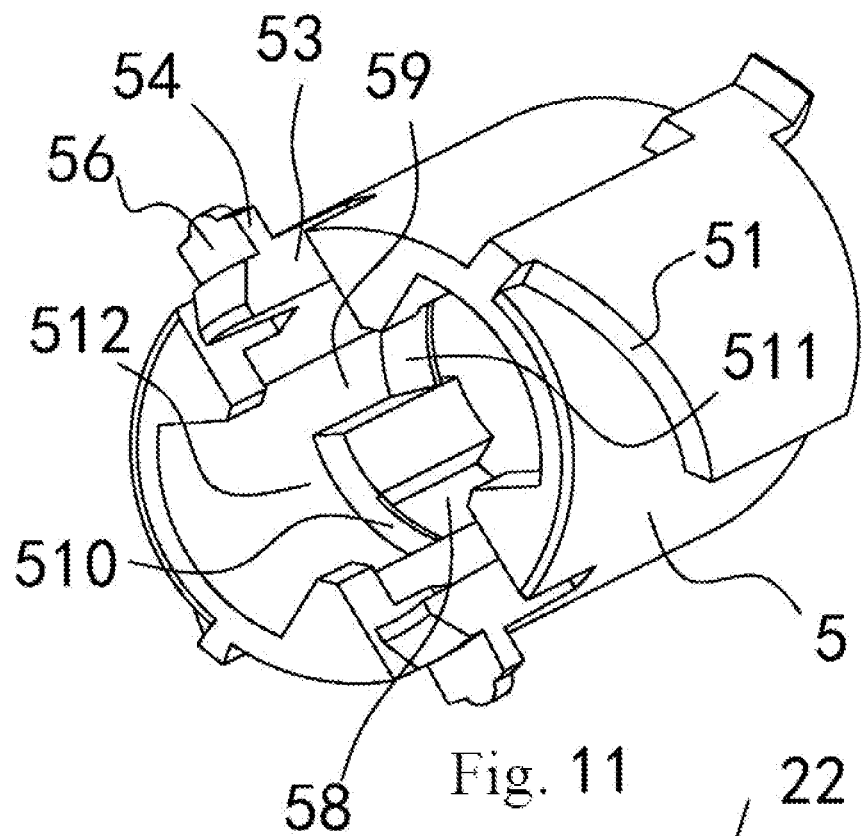
FIG. 11 is the enlarged third perspective view of the rotating tube in the embodiment of present invention.
Figure 12:
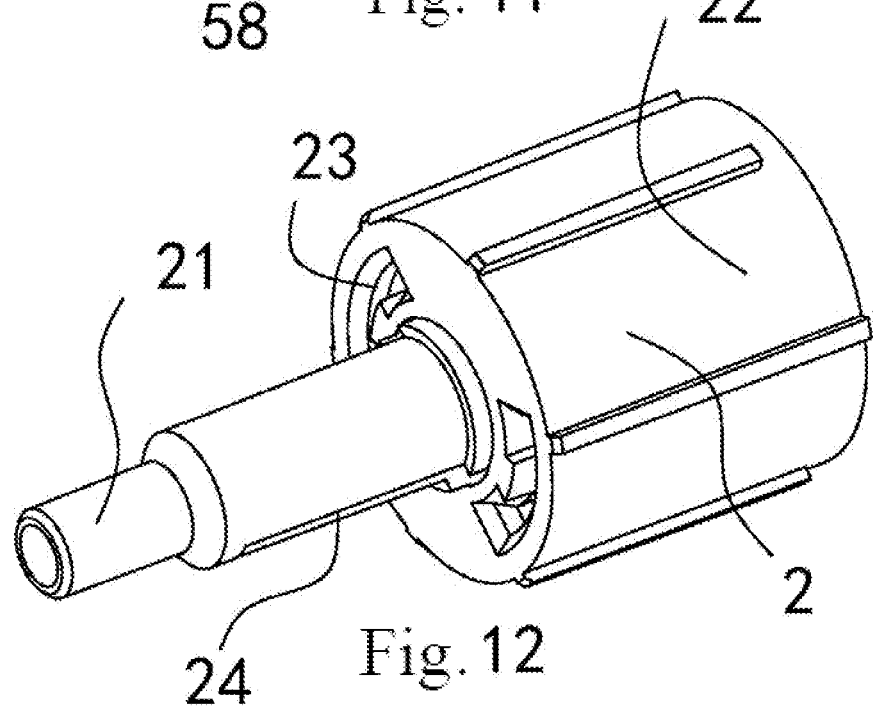
FIG. 12 is the perspective view of threaded shield in an embodiment of present invention.

The main structure of the rotating tube 5 is a tubular body (see FIG. 9-FIG. 11). The ROtating tube 5 is provided with an elastic arm 53 in its front, and the elastic arm 53 is provided with a front protection stopper 54 protruding to the outside of the tubular body, and the front protection stopper is provided with a flange 55 on its top (see FIG. 9 and FIG. 10), and the front end face of the front protection stopper 54 is the front stopping face 56 (see FIG. 9), and the rear end face of the front protection stopper 54 is the rear stopping face 57 (FIG. 10).

The tubular body of the rotating tube 5 is provided with a beveled rail 51 and a straight rail 52 on the outer edge (see FIG. 9 and FIG. 10), and the beveled rail 51 is composed of a section of bevel or spiral face inclined relative to the axis of the tubular body as the guiding face, and the straight rail 52 is composed of a section of straight face parallel to the axis of the tubular body as the guiding face, and the beveled rail 51 is located in the front of the tubular body and the straight rail 52 is located at the rear of the tubular body and the tail of the beveled rail 51 is connected to the head of the straight rail 52.

The tubular body of the rotating tube 5 is provided with a first rail slot 58 and a second rail slot 59 on the inner edge (see FIG. 11). The first rail slot 58 and a second rail slot 59 are arranged in parallel along the axial direction of the tubular body of the rotating tube 5 and are arranged at intervals along the circumferential direction of the tubular body of the rotating tube 5. A transverse channel 512 is arranged circumferentially on the inner edge of the tubular body in the front of the first rail slot 58 and the second rail slot 59.

The first rail slot 58 is provided with a front step 510 in its front (see FIG. 11) and the front step 510 is located in the first rail slot 58, and the front step 510 is composed of a rear bevel and a front abutting face.

The second rail slot 59 is provided with a rear step 511 at its rear end (see FIG. 11) and the rear step 511 is located in the second rail slot 59, and the rear step 511 is composed of a front bevel and a rear abutting face, and the rear end face of the second rail slot 59 is the rear abutting face.

4. Front Shield 4 and Front Spring 7

The front shield 4 is used to protect the injection section of needle body 6 (see FIG. 5-8). The main structure of the front shield 4 is a tubular body.

Figure 8:
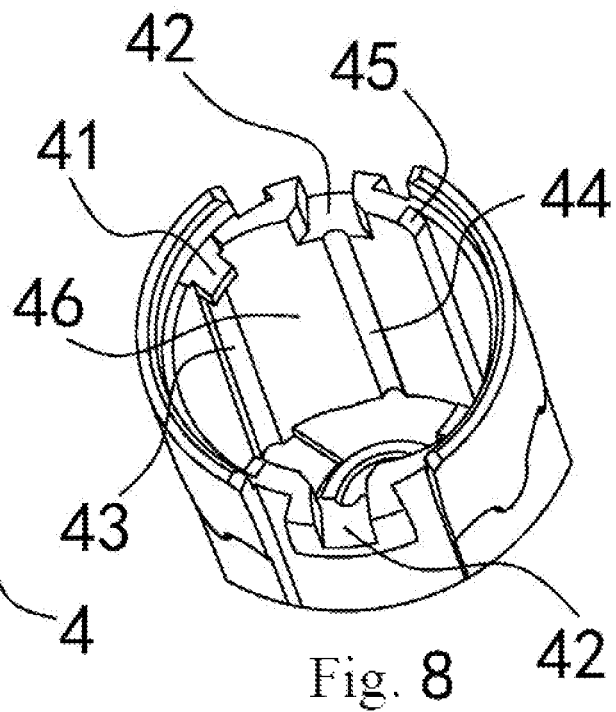
FIG. 8 is a local enlarged view of FIG. 7.

The front shield 4 is provided with a guiding slot 43 and a limit slot 44 on the inner edge of the front shield 4 relative to the front protection stopper 54 on the rotating tube 5 (see FIG. 8). The guiding slot 43 and the limit slot 44 are arranged in parallel along the axial direction of the tubular body of the front shield 4 and are arranged at intervals along the circumferential direction of the tubular body of the front shield 4. A transition face 46 is provided between the guiding slot 43 and the limit slot 44 (see FIG. 8) and the transition face is arc or flat. The distance between the slot base of the guiding slot 43 and the central axis of the front shield 4 is greater than that between the slot base of the limit slot 44 and the central axis of the front shield 4. The guiding slot 43 is provided with a barb 41 at the rear end relative to the rear stopping face 57 of the front protection stopper 54 (see FIG. 8). The limit slot 44 is provided with a stopping face 42 at the rear end relative to the front stopping face 56 of the front protection stopper 54 (see FIG. 8).

The front shield 4 is provided with a bevel acting part 45 on its inner edge relative to the beveled rail 51 on the rotating tube 5 (see FIG. 8).

The front spring 7 is used to coordinate with the front shield 4 and push the front shield 4 to the protection position of the injection section of the needle body 6.

5. Tail Cover 1 and Rear Spring 8

Figures 13, 14:
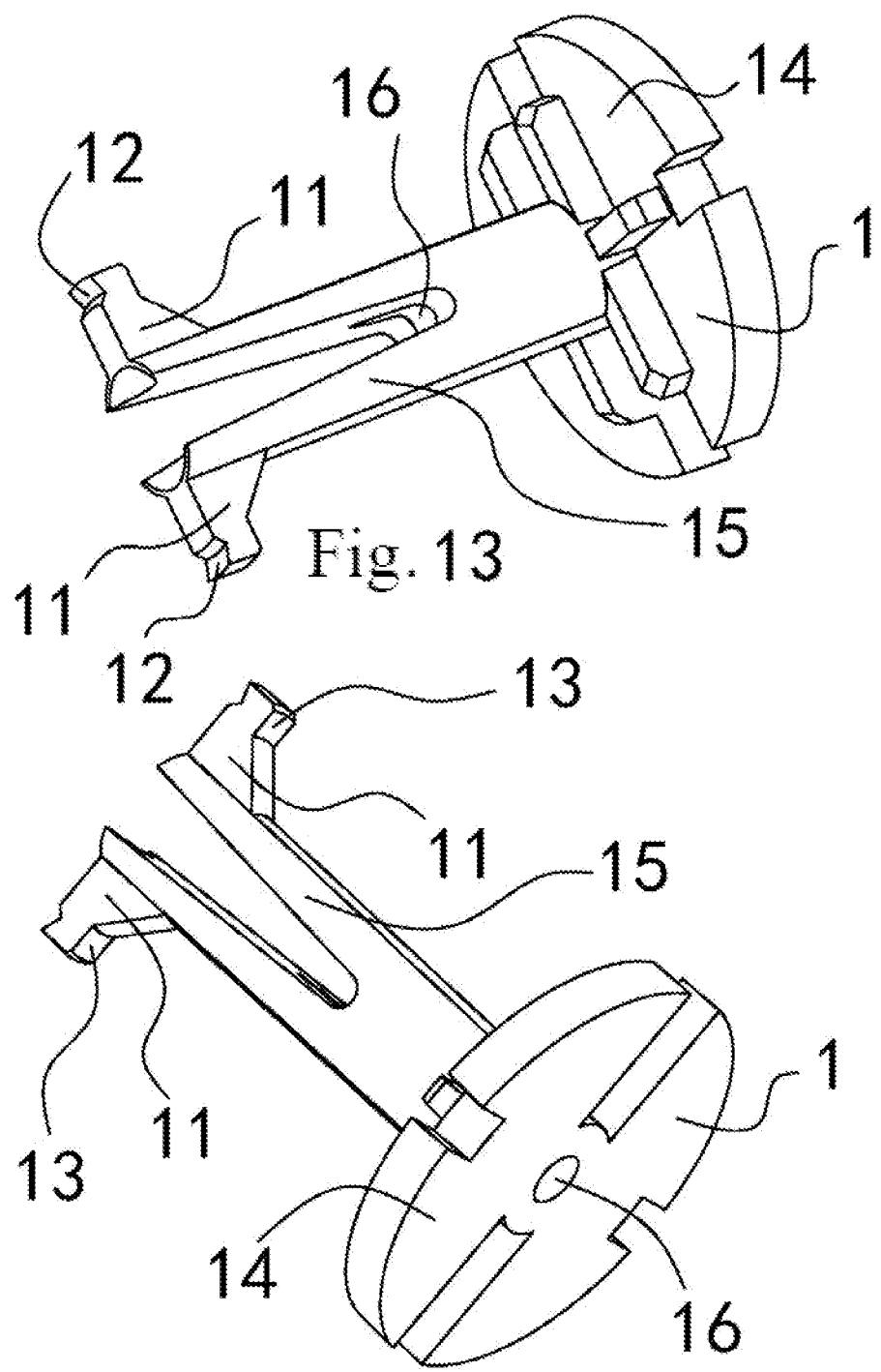
FIG. 13 is the first perspective view of the tail cover of an embodiment of present invention.
FIG. 14 is the second perspective view of the tail cover of an embodiment of present invention.

The tail cover 1 is a component used to protect the connecting section of needle body 6 (see FIG. 13 and FIG. 14). The tail cover 1 is composed of a cap 14 and an elastic leg 15, and the cap 14 is an end cap or a ring body, and the cap 14 is provided with a cannula passing hole 16 only for insertion of the connecting section of the needle body 6 at the center, and the rear part of the elastic leg 15 is fixedly connected with the cap 14, and the elastic leg 15 is provided with a rear protection stopper 11 in the front and the front end face of the rear protection stopper is the front stopping face of rear stopper 12. The rear protection stopper 11 is provided with a rear stopping face of rear stopper 13 relative to the front abutting face of the front step 510.

The rear spring 8 is used to coordinate with the tail cover 1 and push the tail cover 1 to the protection position of the connecting section of the needle body 6.

The following describes the connection and position relationship of the above parts in the assembly state before use:

In the assembly state before use, as shown in FIGS. 15 and 16 (these two figures show the state of the insulin pen being screwed in. In fact, the assembly state before the actual use is the state of not screwing in the insulin pen), the threaded shield 2 is fixed in the intermediate shield 3, and the needle body 6 is located in the intermediate shield 3, and is fixed on the needle base 21 of the threaded shield 2 through the fixing section. The rotating tube 5 is located in the intermediate shield 3, and is positioned and connected relative to the intermediate shield 3 in the axial direction while rotating and connected in the circumferential direction. The specific implementation is: two hooks 513 (see FIG. 9) at the tail of the rotating tube 5 are inserted into the two arc holes 23 on the threaded shield 2 (see FIG. 12 and FIG. 16). At this time, the rotating tube 5 is axially positioned and can be rotated circumferentially. The rear part of the front shield 4 extends into the intermediate shield 3 and is sleeved outside the rotating tube 5 and the front part of the front shield 4 extends out from the through hole at the front end of the intermediate shield 3. The front shield 4 and the intermediate shield 3 are slidably connected in the axial direction. The specific implementation is: The front shield 4 is provided with a sliding channel 47 on the outer edge along the axial direction (see FIGS. 5 and 6), and the sliding channel 47 coordinates with the convex (not marked in the figure) on the inner edge of the intermediate shield 3 to form an axial sliding connection of the front shield 4 relative to the intermediate shield 3. The front shield 4 is provided with a front end limit moving forward relative to the intermediate shield 3. The specific implementation is: the barb 41 on the front shield 4 coordinates with the front protection stopper 54 on the rotating tube 5 to form a front end limit. The front protection stopper 54 on the rotating tube 5 is located in the guiding slot 43 on the inner edge of the front shield 4 and the front protection stopper 54 contacts the guiding slot 43 through the flange 55 on the top. The bevel acting part 45 on the inner edge of the front shield 4 is located on the beveled rail 51. The front spring 7 is sleeved on the outside of the rotating tube 5 and is located in the intermediate shield 3, and the rear end of the front spring 7 is against the frond end face of the shield 22 of the threaded shield 2 (see FIG. 16) and the front end of the spring 7 is against the end face of the front shield 4 (see FIG. 16). The tail cover 1 is located in the threaded shield 2 and the connecting section of the needle body 6 is inserted in the cannula passing hole 16 of the tail cover 1. The elastic leg 5 on the tail cover 1 extends out through the slotted hole 24 on the threaded shield 2 (see FIGS. 12 and 16). The rear protection stopper 11 on the tail cover 1 is located in the first rail slot 58 of the rotating tube 5. The rear spring 8 is located in the intermediate shield 3, and the front end of the rear spring 8 is against the convex part on the inner edge of the rotating tube 5 (not marked in the figure) and the rear end of the rear spring 8 is against the front end face of the elastic leg 15 of the tail cover 1 (see FIG. 16).

The use process of the embodiment is described below:
1. Initial State

Figure 17:
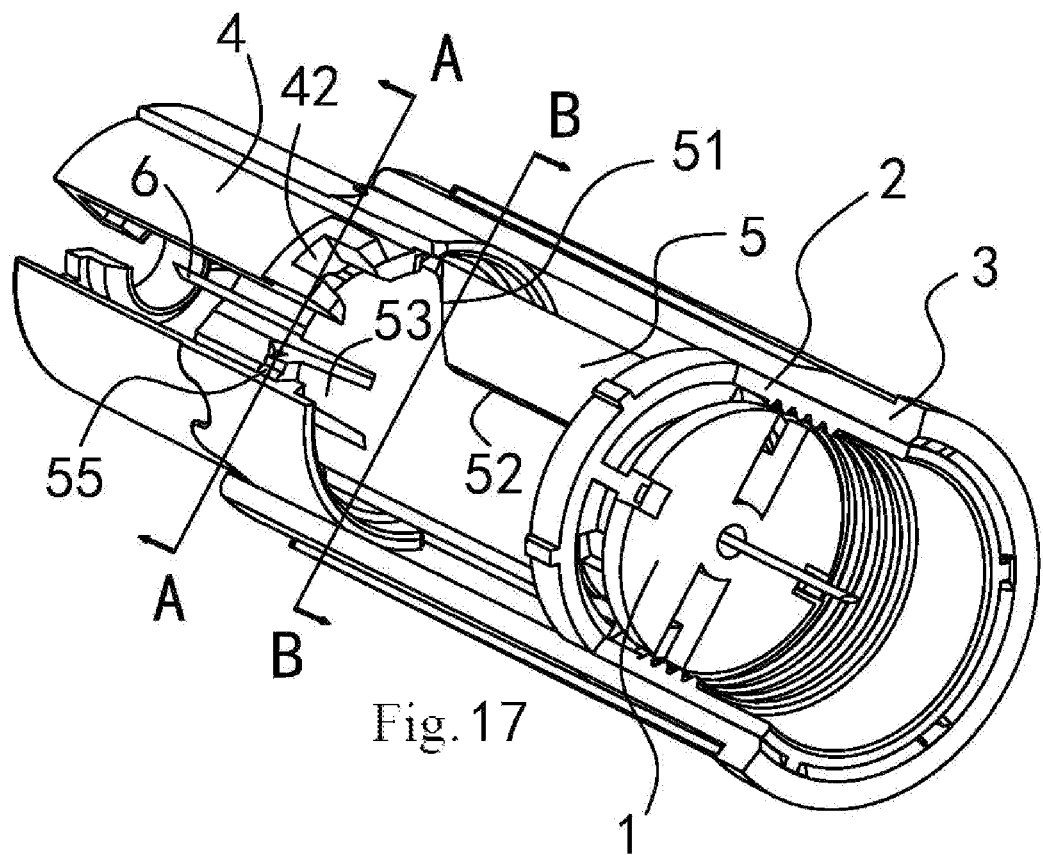
FIG. 17 is another stereoscopic view of an embodiment in initial state of the present invention.
Figure 18:
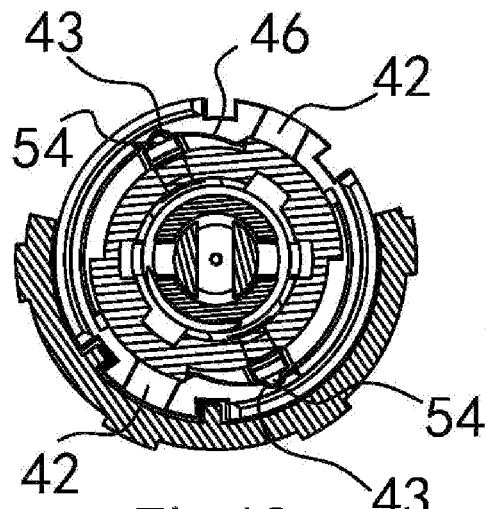
FIG. 18 is the A-A cross sectional view of FIG. 17.
Figure 19:
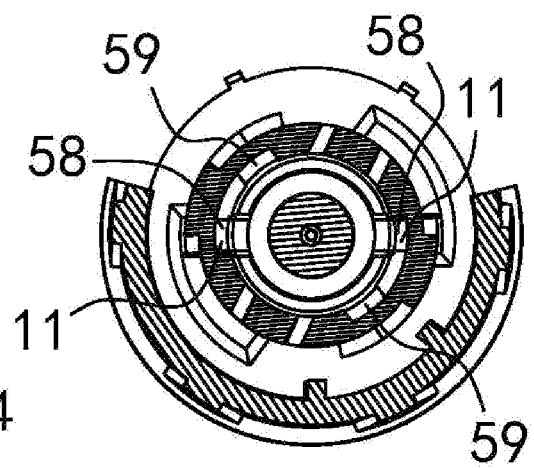
FIG. 19 is the B-B cross sectional view of FIG. 17.

FIG. 15 is the stereoscopic view of an embodiment in initial state of the present invention. FIG. 16 is the section view of an embodiment in initial state of the present invention. FIG. 17 is another stereoscopic view of an embodiment in initial state of the present invention. It can be seen from FIG. 15 to FIG. 17 that the tail cover 1 is in the front end position in this state. FIG. 18 shows A-A section in FIG. 17, and it shows the position and coordination relationship among the front protection stopper 54 on the rotating tube 5 and the guiding slot 43, transition face 46 and stopping face 42 on the front shield 4. It can be seen from FIG. 18 that in this state, the front protection stopper 54 is located in the guide slot 43. FIG. 19 shows B-B section in FIG. 17, and it shows the position and coordination relationship among the rear protection stopper 11 on the tail cover 1 and the first rail slot 58 and second rail slot 59 on the rotating tube 5. It can be seen from FIG. 19 that in this state, the rear protection stopper 11 is located in the first rail slot 58.

2. State of Removing the External Shield

Since the description of the external shield has been abbreviated in the present invention, it is abbreviated here.

3. State of Screwing in the Insulin Pen and Pushing the Insulin Pen Needle

Figure 20:
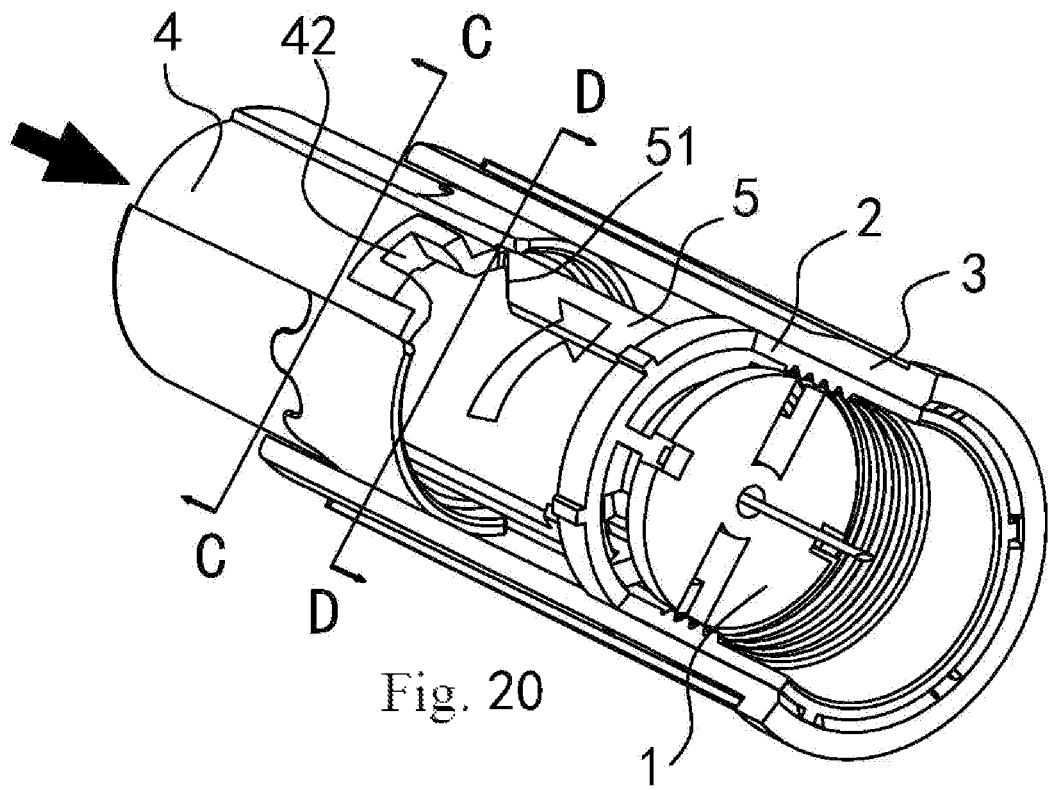
FIG. 20 is the stereoscopic view of an embodiment of the present invention when the insulin pen is screwed in and the front shield is pressed.
Figure 21:
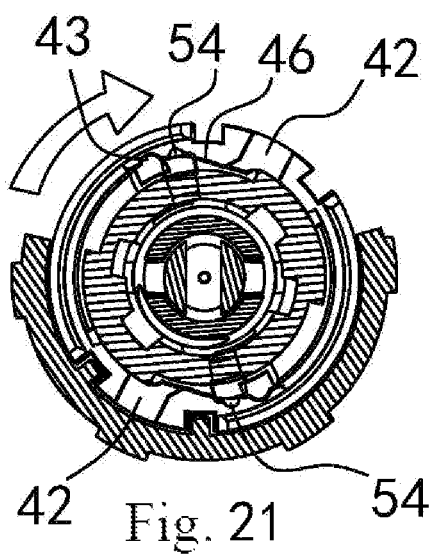
FIG. 21 is the C-C cross sectional view of FIG. 20.
Figure 22:
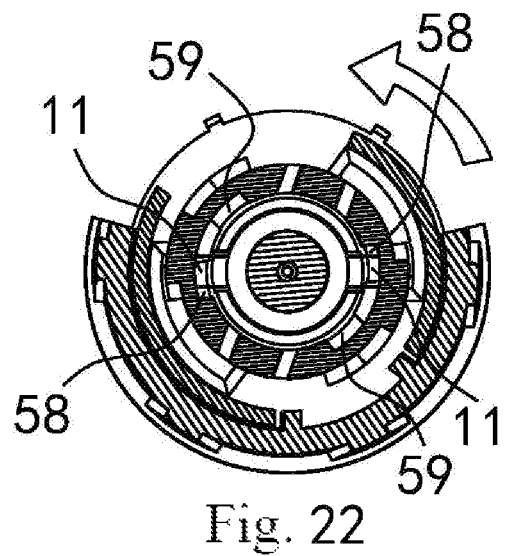
FIG. 22 is the D-D cross sectional view of FIG. 20.

FIG. 20 is the stereoscopic view of an embodiment of the present invention when the insulin pen is screwed in and the front shield is pressed. First screw in the insulin pen at the rear end of the intermediate shield 3 (the screwed insulin pen is hidden in FIG. 20). In such state, when the insulin pen needle is pushed, the front shield 4 contacts skin and the front shield moves backward axially relative to the intermediate shield 3, and the bevel acting part 45 on the inner edge of the front shield 4 and the beveled rail 51 on the outer edge of the rotating tube 5 coordinate with each other to force the rotating tube 5 to rotate in the circumferential direction relative to the front shield 4, and the front protection stopper 54 on the rotating tube 5 transversely slides to the limit slot 44 from the inner edge of the guiding slot 43 of the front shield 4 via the transition face 46. At the same time, the rear protective stopper 11 on the elastic leg 15 of the tail cover 1 slides laterally from the first rail slot 58 along the transverse channel 512 to the second rail slot 59. FIG. 21 shows C-C section in FIG. 20, and it shows the position and coordination relationship among the front protection stopper 54 on the rotating tube 5 and the guiding slot 43, transition face 46 and stopping face 42 on the front shield 4. It can be seen from FIG. 21 that in this state, the front protection stopper 54 on the rotating tube 5 has left the guiding slot 43 on the front shield and slides to the limit slot 44. FIG. 22 shows D-D section in FIG. 20, and it shows the position and coordination relationship among the rear protection stopper 11 on the tail cover 1 and the first rail slot 58 and second rail slot 59 on the rotating tube 5. It can be seen from FIG. 22 that in this state, the rear protection stopper 11 on the tail cover 1 has left the first rail slot 58 on the rotating tube 5 and slides to the second rail slot 59.

4. State of Penetrating into Skin

FIG. 23 is the stereoscopic view of an embodiment of the present invention when the front shield is continuously pressed until the needle tip penetrates into the skin. In such state, continue to push the insulin pen needle and the bevel acting part 45 on the front shield 4 contacts the straight rail 52 on the rotating tube 5, and at this time, the rotating tube 5 doesn't rotate anymore, so the front protection stopper 54 on the rotating tube 5 slides backward in the limit slot 44. When the insulin pen needle is pushed to the bottom, the front end of the front shield 4 is flush with the front end of the intermediate shield 3, indicating the completion of the penetrating action. FIG. 24 is the E-E section view in FIG. 23. It can be seen from FIG. 24 that in this state, the front protection stopper 54 on the rotating tube 5 is already located in the limit slot 44. FIG. 25 is the F-F section view in FIG. 23. It can be seen from FIG. 25 that in this state, the rear protection stopper 11 on the tail cover 1 is already located in the second rail slot 59.

5. State After the Needle is Pulled Out of Skin After the Insulin Injection

Figure 26:
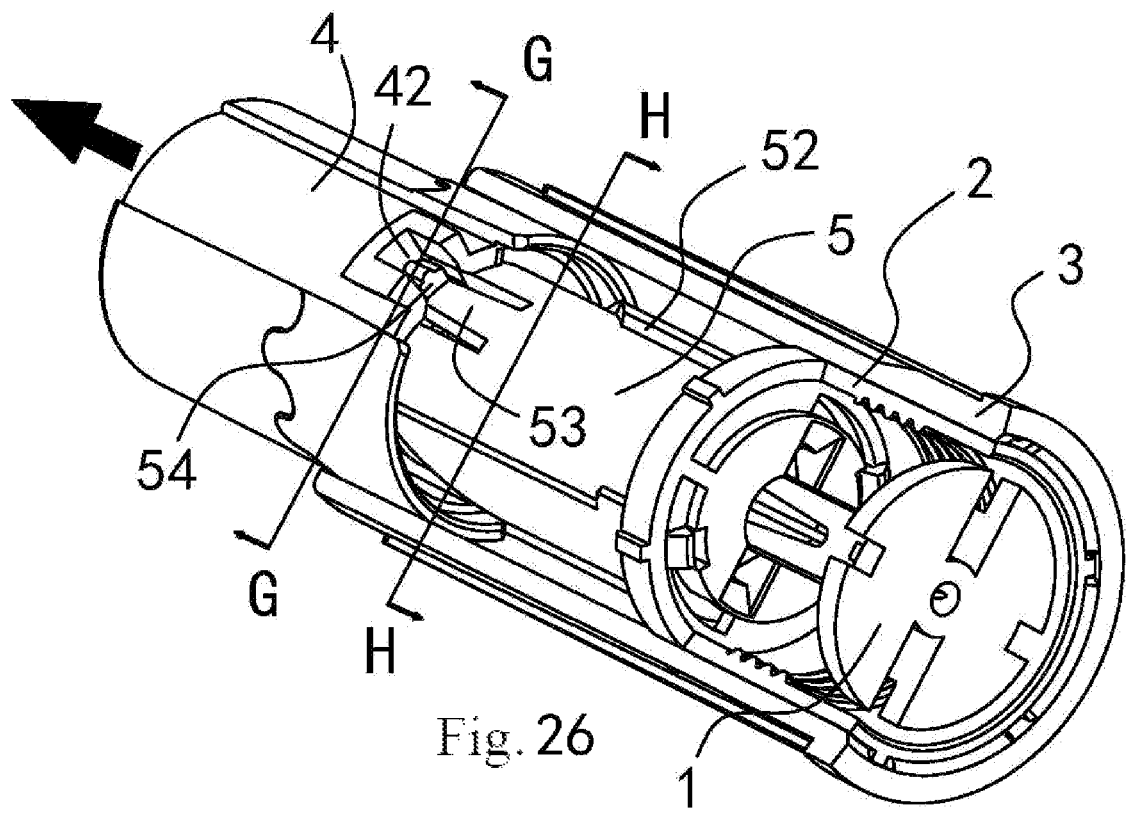
FIG. 26 is the stereoscopic view of an embodiment of the present invention after it's pulled out of skin
Figure 27:
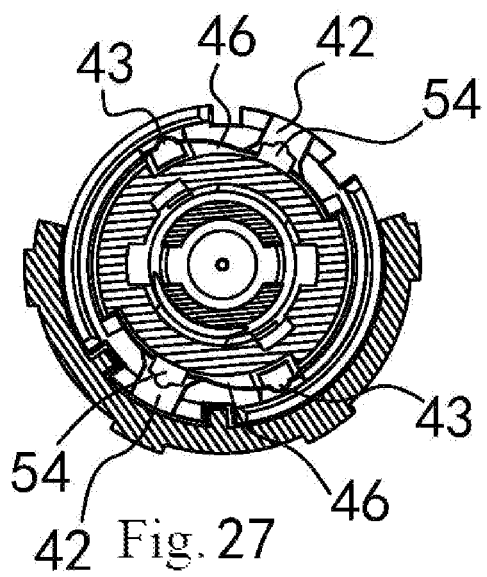
FIG. 27 is the G-G cross sectional view of FIG. 26.

FIG. 26 is the stereoscopic view of an embodiment of the present invention after it's pulled out of skin In such state, the front spring 7 pushes the front shield 4 forward, and when the front shield 4 moves to the front end limit position relative to the intermediate shield 3, the front protection stopper 54 upsprings, and at this time, the front stopping face 56 of the front protection stopper 54 is against the stopping face 42 of the front shield 4, so that the front shield 4 is axially positioned relative to the intermediate shield 3 and enters the front-end protection state. FIG. 27 is the G-G section view in FIG. 26. It can be seen from FIG. 27 that in this state, the front protection stopper 54 on the front shield 4 upsprings, and the front stopping face 56 on the front protection stopper 54 is against the stopping face 42 on the front shield 4 and the front shield 4 enters the front-end protection state and can't be pressed into the intermediate shield 3 again.

6. State of Removing from the Insulin Pen

Figure 28:
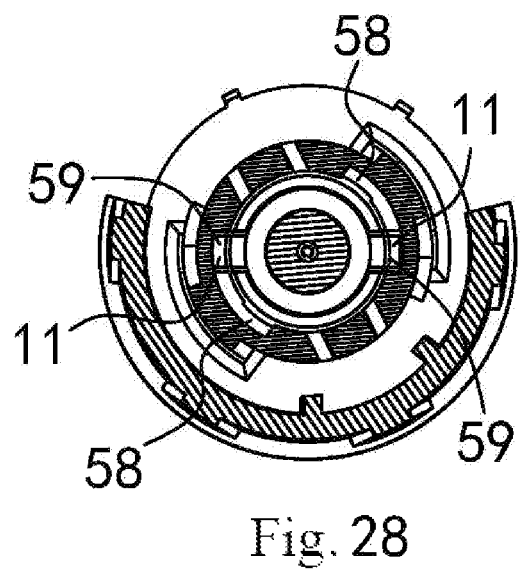
FIG. 28 is the H-H cross sectional view of FIG. 27.

FIG. 26 is also the stereoscopic view of state of removing from the insulin pen. When the insulin pen is screwed to remove the insulin needle, the rear spring 8 pushes the tail cover 1 to move backward and at the same time, the rear protection stopper 11 on the elastic leg 15 of the tail cover 1 moves backward along the second rail slot 59. When the rear protection stopper 11 moves backward to the rear end limit position along the second rail slot 59, the rear protection stopper 11 climbs the front bevel of the rear step 511 and crosses the rear step 511, and the rear protection stopper 11 upsprings, and at this time, the front stopping face of rear stopper 12 on the rear protection stopper 11 is against the rear abutting face of the rear step 511 at the rear end of the second rail slot 59, so that the tail cover 1 is axially positioned relative to the intermediate shield 3 and enters the rear-end protection state. FIG. 28 is the H-H section view in FIG. 27. It can be seen from FIG. 28 that in this state, the rear protection stopper 11 on the tail cover 1 is located in the second rail slot 59 on the rotating tube 5. FIG. 29 is the section view of an embodiment of the present invention when it's pulled out of the skin and removed from the insulin pen.

The content and change of the above embodiment is as follows:

1. In the above embodiment, the beveled rail 51 is formed by a guiding face on the outer edge of the rotating tube 5, and the bevel acting part 45 is a convex relative to the guiding face and the convex is slidably contacted and coordinated relative to the guiding face to change the axial backward movement of the front shield 4 relative to the intermediate shield 3 to the circumferential rotation of the rotating tube 5 relative to the intermediate shield 3. However, the invention is not limited to this, and the beveled rail 51 can also be formed by two guiding faces on the outer edge of the rotating tube 5, and two guiding faces form a guiding slot, and the bevel acting part 45 is a lug relative to the guiding slot, and the lug is located in the guiding slot and is slidably contacted and coordinated relative to the guiding channel to change the axial backward movement of the front shield 4 relative to the intermediate shield 3 to the circumferential rotation of the rotating tube 5 relative to the intermediate shield 3. It can be understood by those skilled in the art.

2. In the above embodiment, the intermediate shield 3 and the threaded shield are separated structures and then they are integrated through the set combination, which is designed for the consideration of processing technology. From the perspective of construction and structure, the intermediate shield 3 and the threaded shield 2 can be designed as an integral structure without affecting the technical effect of the invention, which can be understood by those skilled in the art.

3. In the above embodiment, it can be seen from the drawings that the number of structures such as beveled rail 51, straight rail 52, elastic arm 53, front protection stopper 54, first rail slot 58 and second rail slot 59 on rotating tube 5 is two symmetrically arranged in circumferential direction, but the invention is not limited to this, and the number of these structures can be designed to be one, three, four, five or even more, and the number of two is just the optimal design. All these structures are evenly distributed in the circumferential direction of the rotating tube 5. This is a change that can be understood by those skilled in the art.

4. In the above embodiment, it can be seen from the drawings that the number of structures such as barb 41, stopping face 42, guiding slot 43, limit slot 44, bevel acting part 45, transition face 46 and sliding channel 47 on the front shield 4 is two symmetrically arranged in circumferential direction, but the invention is not limited to this, and the number of these structures can be designed to be one, three, four, five or even more, and the number of two is just the optimal design. All these structures are evenly distributed in the circumferential direction of the front shield 4. This is a change that can be understood by those skilled in the art.

5. In the above embodiment, it can be seen from the drawings that the number of structures such as elastic leg 15 and rear protection stopper 11 on the tail cover 1 is two symmetrically arranged in circumferential direction, but the invention is not limited to this, and the number of these structures can be designed to be one, three, four, five or even more, and the number of two is just the optimal design. All these structures are evenly distributed in the circumferential direction of the tail cover 1. This is a change that can be understood by those skilled in the art.

6. In the above embodiment, it can be seen from the FIG. 15-17 that the tail cover 1 is located in the front end position before it's loaded into the insulin pen. The invention is not limited to this and the tail cover 1 can also be located in the middle position or rear end position before it's loaded into the insulin pen. When the tail cover 1 is located in the rear end position and when the insulin pen is screwed in the threaded shield 2 from the rear end of the intermediate shield 3, the head of the insulin pen pushes the tail cover 1 to axially move forward relative to the intermediate shield 3, and at this time, the rear protection stopper 11 on the elastic leg 15 of the tail cover 1 moves forward along the first rail slot 58 of the rotating tube 5. When the rear protection stopper 11 moves to the front end of the first rail slot 58, the rear protection stopper 11 climbs the rear bevel of the front step 510 and crosses the front step 510 to reach the transverse channel 512, and at this time, the rear stopping face of rear stopper on the rear protection stopper 11 is against the front abutting face on the front step 510, so that the tail cover 1 can't be returned under the action of the rear spring 8.

7. In the above embodiment, in the assembly state before use, the rear spring 8 is located in the intermediate shield 3 and the front end of the rear spring 8 is positioned relative to the intermediate shield 3 and the rear end of the rear spring 8 is against the tail cover 1. However, the invention is not limited to this and in the assembly state before use, the rear spring 8 can also be located in the rotating tube 5 and the front end of the rear spring 8 is positioned relative to the intermediate shield 5 and the rear end of the rear spring 8 is against the tail cover 1.

It should be noted that the above described embodiments are only for illustration of technical concept and characteristics of present invention with purpose of making those skilled in the art understand the present invention, and thus these embodiments shall not limit the protection range of present invention. The equivalent changes or modifications according to spiritual essence of present invention shall fall in the protection scope of present invention.

The invention claimed is:

1. A safety insulin pen needle comprising:
    a needle body with an injection section at a front end of the needle body and a connecting section at a rear end of the needle body;
    an intermediate shield that has a tube structure, the intermediate shield being provided with a through hole at a front end of the intermediate shield and being connected to, or provided with a connector configured to connect to, an insulin pen at a rear end of the intermediate shield;
    a front shield that protects the injection section of the needle body, a main structure of the front shield being a tubular body;
    a tail cover that protects the connecting section of the needle body;
    a rear spring that pushes the tail cover to a protection position at which the tail cover protects the connecting section of the needle body; and
    a rotating tube, a main structure of the rotating tube being a tubular body, an outer edge of the tubular body of the rotating tube being provided with a beveled rail, the beveled rail being composed of a section of bevel or spiral surface as a guiding surface; wherein:
    an inner edge of the front shield is provided with a bevel acting part that interacts with the beveled rail on the rotating tube;
    the tail cover is composed of a cap and an elastic leg, the cap is an end cap or a ring body, a center of the cap is provided with a cannula passing hole configured for insertion of the connecting section of the needle body, a rear part of the elastic leg is fixedly connected with the cap, a front of the elastic leg is provided with a rear protection stopper, and a front end face of the rear protection stopper is a front stopping face;
    an inner edge of the tubular body of the rotating tube is provided with a first rail slot and a second rail slot that interact with the rear protection stopper on the elastic leg of the tail cover, and the first rail slot and the second rail slot are arranged in parallel along an axial direction of the tubular body of the rotating tube and are spaced apart along a circumferential direction of the tubular body of the rotating tube;
    a transverse channel is arranged circumferentially on the inner edge of the tubular body of the rotating tube in front of the first rail slot and the second rail slot;
    in an assembly state before use,
        the needle body is located in the intermediate shield, and is fixed relative to the intermediate shield;
        the rotating tube is located in the intermediate shield, is axially positioned and connected relative to the intermediate shield, and is configured to be circumferentially rotatable;
        a rear part of the front shield extends into the intermediate shield and is sleeved outside the rotating tube, a front part of the front shield extends out of the through hole at the front end of the intermediate shield, the front shield and the intermediate shield are slidably connected in the axial direction, and the front shield is provided with a front end limit that limits forward movement of the front shield relative to the intermediate shield;
        the bevel acting part on the inner edge of the front shield is located on the beveled rail;
        the tail cover is located in the intermediate shield and the connecting section of the needle body is inserted in the cannula passing hole of the cap of the tail cover;
        the rear protection stopper of the elastic leg of the tail cover is located in the first rail slot of the rotating tube; and
        the rear spring is located in the intermediate shield, a front end of the rear spring is positioned relative to the intermediate shield or the rotating tube, and a rear end of the rear spring pushes against the tail cover; and
    in a use state,
        when the insulin pen needle is pushed, the front shield moves backward axially relative to the intermediate shield, and the bevel acting part on the inner edge of the front shield and the beveled rail on the outer edge of the rotating tube interact with each other to force the rotating tube to rotate in the circumferential direction relative to the front shield, and the rear protection stopper on the elastic leg of the tail cover slides laterally to the second rail slot along the transverse channel;
        when the insulin pen exits the intermediate shield, the rear spring pushes the tail cover to move backward, and at the same time, the rear protection stopper on the elastic leg of the tail cover moves backward along the second rail slot; and
        when the rear protection stopper moves backward along the second rail slot to a rear end limit position, the rear protection stopper deflects outward, and at this time, the front stopping face of the rear protection stopper is against a rear end face of the second rail slot, so that the tail cover is axially positioned relative to the intermediate shield and enters a rear-end protection state.

2. The safety insulin pen needle according to the claim 1, wherein: the second rail slot is provided with a rear step at its rear end and the rear step is located in the second rail slot, and the rear step is composed of a front bevel and a rear abutting face, and the rear end face of the second rail slot is the rear abutting face.

3. The safety insulin pen needle according to the claim 1, wherein:
    a front of the first rail slot is provided with a front step and the front step is located in the first rail slot, the front step is composed of a rear bevel and a front abutting face;
    the rear protection stopper is provided with a rear stopping face that interacts with the front abutting face; and
    when the rear protection stopper moves forward along the first rail slot of the rotating tube, the rear protection stopper climbs the rear bevel and crosses the front step, and the rear stopping face of the rear protection stopper is against the front abutting face on the front step, so that the tail cover can't be returned under the action of the rear spring.

4. The safety insulin pen needle according to the claim 1, further comprising a front spring that pushes the front shield to a protection position at which the front shield protects the injection section of the needle body, wherein:
   a front of the rotating tube is provided with an elastic arm, the elastic arm is provided with a front protection stopper protruding outside of the tubular body of the rotating tube, a top of the front protection stopper is provided with a flange, and a front end face of the front protection stopper is a front stopping face;
   an inner edge of the front shield is provided with a guiding slot and a limit slot that interact with the front protection stopper of the rotating tube, and the guiding slot and the limit slot are arranged in parallel along the axial direction of the tubular body of the front shield and are spaced apart along the circumferential direction of the tubular body of the front shield; and
   a rear end of the limit slot is provided with a stopping face that abuts against the front stopping face of the front protection stopper.

5. The safety insulin pen needle according to the claim 4, wherein: a transition face is provided between the guiding slot and the limit slot on the inner edge of the front shield, and the transition face is arcuate or flat.

6. The safety insulin pen needle according to the claim 5, wherein: a distance between a slot base of the guiding slot and a central axis of the front shield is greater than that between a slot base of the limit slot and the central axis of the front shield.

7. The safety insulin pen needle according to the claim 4, wherein: a rear end of the guiding slot is provided with a barb that abuts against a rear stopping face of the front protection stopper.

8. The safety insulin pen needle according to the claim 1, wherein: an outer edge the tubular body of the rotating tube is provided with a straight rail, and the straight rail is composed of a section of straight face parallel to the axis of the tubular body of the rotating tube as a guiding face, the beveled rail is located at a front of the tubular body of the rotating tube and the straight rail is located at a rear of the tubular body of the rotating tube, and a tail of the beveled rail is connected to a head of the straight rail.

* * * * *